(12) United States Patent
Brabrand et al.

(10) Patent No.: US 6,443,960 B1
(45) Date of Patent: Sep. 3, 2002

(54) APPARATUS FOR LIGHT BEAM GUIDED BIOPSY

(75) Inventors: Knut Brabrand, Rasta; Ole Henrik Eriksen; Ørjan Låg, both of Oslo; Jan Martin Bendiksen, Drammen-Rødhetteun; Dag Almar Hansen, Sandefjord; Steinar Småstuen, Oslo, all of (NO)

(73) Assignee: NeoRad A/S, Oslo (NO)

( * ) Notice: Subject to any disclaimer, the term of this patent is extended or adjusted under 35 U.S.C. 154(b) by 7 days.

(21) Appl. No.: 09/784,627

(22) Filed: Feb. 15, 2001

(30) Foreign Application Priority Data

Nov. 24, 2000 (NO) ............................................. 20005975

(51) Int. Cl.$^7$ .............................. A61B 5/00; A61B 19/00
(52) U.S. Cl. ..................... 606/130; 600/429; 600/562; 600/427; 606/130
(58) Field of Search ................. 600/407, 427, 600/411, 417, 429, 562, 130; 378/206

(56) References Cited

U.S. PATENT DOCUMENTS

| | | | | |
|---|---|---|---|---|
| 5,531,031 A | * | 7/1996 | Green ........................ 33/365 |
| 5,598,269 A | | 1/1997 | Kitaevich et al. | |
| 5,792,215 A | | 8/1998 | Martin et al. | |
| 5,987,349 A | * | 11/1999 | Schulz ...................... 600/427 |
| 6,021,342 A | | 2/2000 | Brabrand | |
| 6,044,291 A | * | 3/2000 | Rockseisen ................ 600/429 |
| 6,314,650 B1 | * | 11/2001 | Falb ........................... 33/286 |
| 6,334,067 B1 | * | 12/2001 | Brabrand ................... 600/427 |

FOREIGN PATENT DOCUMENTS

DE          4412164          4/1994

* cited by examiner

*Primary Examiner*—Marvin M. Lateef
*Assistant Examiner*—DevaanG Shah
(74) *Attorney, Agent, or Firm*—Barry R. Lipsitz; Douglas M. McAllister

(57) ABSTRACT

An apparatus for assisting percutaneous light beam guided biopsy, having means for rotating a laser device about first and second rotation axes, the laser device providing its laser beam along an axis intersecting an intersection point between the first and second rotation axes and at right angles thereto.

Inclinometers are installed for providing signal values as a function of two- or three-dimensional orientation directions of the said laser device relative to direction of gravitation. Encoding means provide feedback of rotary position information of the laser device. Comparing means compare set calculated instrument insertion angle values, provided from an input device, with encoder feedback signals and inclinometer signals and inhibits rotation operation of the laser device upon reaching specific threshold values.

23 Claims, 8 Drawing Sheets

APPARATUS FOR LIGHT BEAM GUIDED BIOPSY

BACKGROUND OF THE INVENTION

The present invention relates to an apparatus for assisting percutaneous light beam guided surgical activity into a human or animal body based on calculated craniocaudal and transverse related insertion angles for an injection instrument, such as a syringe needle or biopsy means, relative to a target inside said body, said apparatus having means for providing at least a laser beam from a laser device in a laser unit for assisting guided instrument injection into said body, said laser unit having a housing being positionable along a laser unit supporting means and lockable thereto, said laser unit having means for adjusting the direction of said laser beam relative to said body based on said calculated insertion angles.

Prior art apparatus of this type are known from e.g. U.S. Pat. No. 5,628,327 (Unger et al) and U.S. Pat. No. 6,021,342 (Brabrand).

U.S. Pat. No. 5,628,327 describes a device which is complicated to operate due to risk of angle errors relative to craniocaudal direction and transverse direction as well as direction of gravity.

U.S. Pat. No. 6,021,342, relative to which the present invention is an improvement, provides an apparatus for manually adjusting insertion angles. The apparatus has no means for compensating any laser device direction deviations away from direction of gravity, which in certain cases could cause insertion angle problems.

SUMMARY OF THE INVENTION

The present invention intends to provide an apparatus which based on calculated, craniocaudal and transverse related insertion angles for the injection instrument is capable of fully automatically directing the laser beam of the laser device along the correct laser beam direction, thus indicating in the first hand the insertion point on the body of the patient, and secondly upon placing the point of the instrument needle thereat, pointing the beam at a rear end of the instrument for the laser beam guided insertion. Further, based on the set calculated instrument insertion angle values, provided from an input device, the insertion angle values being calculated by e.g. a computed tomography unit or a magnetic resonance tomography unit, it is the intention of the invention that the apparatus is able of using such input values to cause the laser device to provide accurately the positioning of the laser beam without any risk of errors caused e.g. by errors due to deviations from directions of gravitation of the laser unit housing.

According to the invention, the apparatus comprises within said laser unit housing:
first attachment means on said laser unit housing for rotatably supporting a first rotation member of said laser unit,
first rotation means attached to said first attachment means for rotating said first rotation member relative to said first attachment means about a first rotation axis,
second attachment means attached to said first rotation member for rotatably supporting a second rotation member, said second rotation member having a second rotation axis at right angles to the first rotation axis,
second rotation means mounted on said first rotation member for rotating said second rotation member relative to said second attachment means,
first and second inclinometer supporting means mounted at right angles to each other and attached to a surface of said second rotation member at right angles thereto,
said laser unit having said laser device attached to said second rotation member in such a way that the laser beam is along an axis intersecting an intersection point between said first and second rotation axis and at right angles thereto,
first inclinometer means installed on said first inclinometer supporting means and second inclinometer means installed on said second inclinometer supporting means, said inclinometer means providing signal values as a function of two- or three dimensional orientation directions of said laser unit housing relative to direction of gravitation,
first and second encoder means cooperative with said first and second rotation means, respectively for feedback of rotary position information thereof, and comparator means for comparing set calculated instrument insertion angle values, provided from an input device, with encoder signal values derived from said feedback information and said inclinometer signal values, said comparator means inhibiting an operation of said first and second rotation means when said encoder signal values and said inclinometer signal values reach threshold values, respectively related to said set insertion angle values and direction of gravitation.

According to the invention a line laser unit having a line laser device is provided, said line laser device providing a laser beam created line for aligning said laser unit housing relative to a craniocaudal direction of a movable bed supporting said body. Thereby, it may be established that e.g. a substantially horizontal laser unit supporting means is extending in direction exactly transverse to said craniocaudal direction. Suitably, said laser device is mounted on said first or second inclinometer supporting means. Further, said line laser device can be mounted on said first or second inclinometer supporting means. Preferably, but not necessarily, said laser device and said line laser device are mechanically rigidly interconnected.

In one embodiment of the present invention, said first and second rotation members have suitably a fixed radius of curvature over at least a substantial part of a circumference thereof, respectively, wherein said first and second rotation means each comprises an electric motor and a shaft thereof, said shaft capable of being in a rotational, frictional engagement with at least a substantial part of said circumference. In order to provide for such an embodiment, said shaft may be provided with a friction creating material. As an alternative or as an added feature, said substantial part of said circumference may be provided with a friction creating material.

Suitably, said frictional engagement is adjustable or maintained through said stepper motor shaft resiliently bearing against said substantial part of the circumference.

In an alternative, said first and second rotation members have a fixed radius of curvature over the full circumference thereof, respectively, wherein said first and second rotation means each comprises an electric motor and a shaft thereof, said shaft capable of being in rotational, frictional engagement with a belt in contact with a substantial part of said circumference.

In a further alternative, said first and second rotation members have a fixed radius of curvature over at least a substantial part of a circumference thereof and have gear teeth extending therealong, respectively, wherein said first and second rotation means each comprises an electric motor and a shaft thereof, said shaft having a gear, capable of being in rotational, frictional engagement with said gear teeth. In still another alternative, said first and second rotation members are each directly connected to a stepper motor shaft.

Suitably, said first and second inclinometer supporting means are circuit board members mounted at right angles to each other and attached to a surface of said second rotation member at right angles thereto, one of said circuit board members having hole means for laser beam exit from said laser device.

Said line laser device is suitably attached to said second rotary member or to one of said inclinometer supporting means.

Said electric motor means is suitably a stepper motor.

In another aspect of the invention, the apparatus further comprises releasable brake means within said laser unit housing, said brake means being in the form of roller means rotatably bearing against and position-fixable relative to a profiled face of said laser unit housing supporting means, and position adjustment means for fine adjustment for a position of said laser unit housing on said supporting means.

In still a further embodiment said laser unit housing supporting means comprises a movable base member, being position lockable relative to a floor, an upright, first housing supporting member extending upwardly from said base member, and a second housing supporting member extending from a top of said first housing supporting member at right angles thereto, and a curved transition member extending between said first and second laser unit housing supporting members for supporting the laser unit and its housing in movement between said first and second head supporting means, whereby said laser unit housing is movable along said first and second head supporting members and selectively lockable thereto.

Suitably said first laser unit housing supporting member is pivotable about its vertical axis relative to said base member, and lockable thereto.

BRIEF DESCRIPTION OF THE DRAWINGS

The invention is now to be further described with reference to the drawings showing non-limiting, preferred embodiments of the present invention.

DETAILED DESCRIPTION OF THE INVENTION

Figure 1:
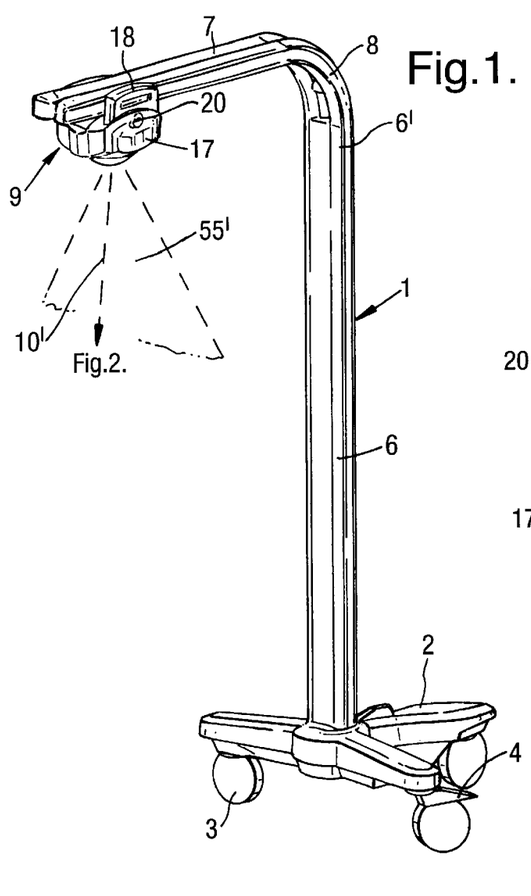
FIG. 1 shows the overall apparatus, according to the invention in a preferred embodiment thereof.
Figure 3:
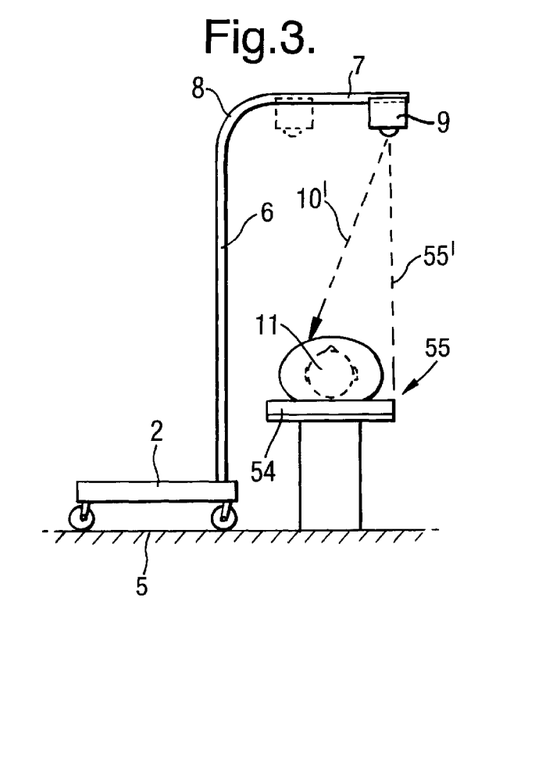
FIG. 3, 4 and 5 show applications of the present invention.

FIG. 1 shows a typical apparatus for assisting percutaneous light ray guided surgical activity into a human or animal body based on craniocaudal and transverse related insertion angles for an injection instrument calculated from computed tomography or magnetic resonance tomography based tests using a CT or MR apparatus or any similar type of apparatus. As noted on FIG. 1 the apparatus, denoted by reference numeral 1 has a movable base member 2 movable on casters 3, said casters having a locking mechanism 4 for locking relative to a floor 5. The apparatus has an upright first housing supporting member 6 extending upwardly from the base member 2, and a second housing supporting member 7 extending from a top region 6' of the first housing supporting member and at right angles thereto, and a curved transition member 8 which extends between the first and second laser unit housing supporting members 6, 7 for supporting a laser unit and its housing, denoted by reference numeral 9 in a movement between the first and second head supporting means 6, 7. Thereby, as indicated by e.g. FIGS. 3 and 4, the laser unit housing 9 will be movable along said first and second head supporting members, suitably via said transition member, and being selectively lockable thereto. As shown on FIG. 5, the first laser unit housing supporting member 6 is suitably pivotable about its axis relative to the base member 2 and lockable thereto. This means, as shown, that the apparatus may be stored using a minimum of available space.

Figure 4:
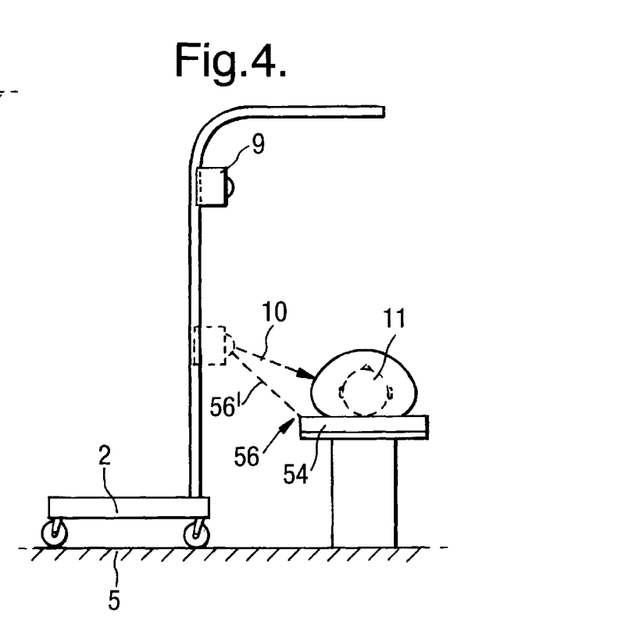
Figure 5:
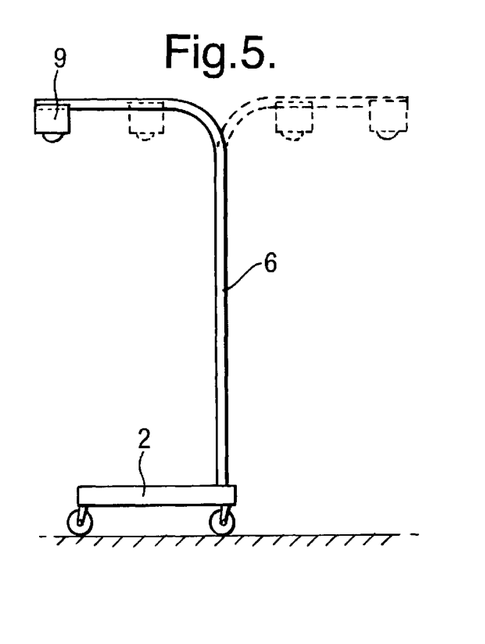

Further, it should be noted, as shown on FIG. 4 that by moving the laser unit housing 9 from the supporting member 7 down to the supporting member 6, it will be possible to have a guiding laser beam 10 pointing to a side of patient I1 instead of having to always use an insertion from above, as indicated by the laser line 10'.

Figure 2:
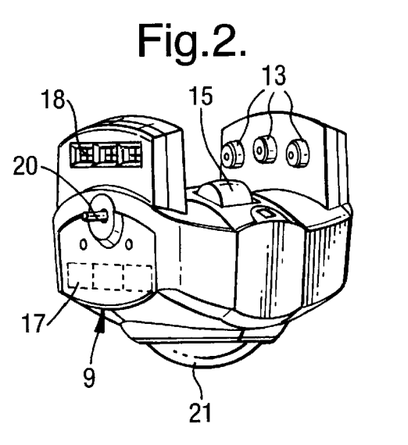
FIG. 2 shows a laser unit with a laser unit housing, according to the invention.
Figure 6:
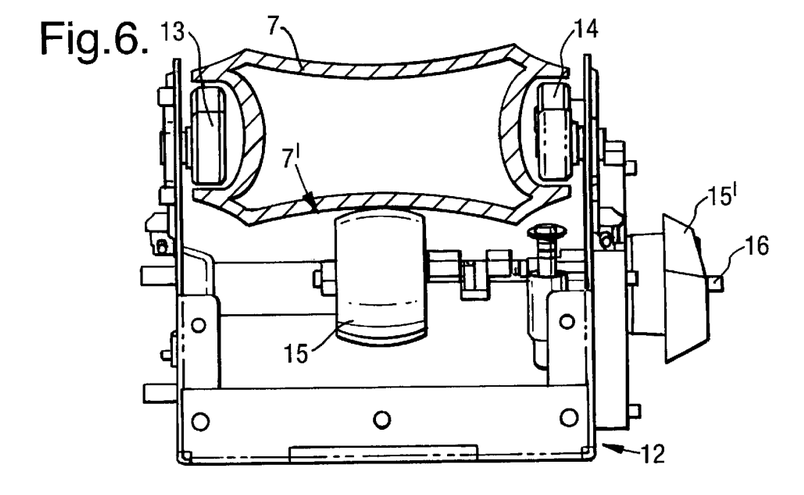
FIG. 6 shows in a partly sectional view part of the laser unit housing and a laser unit supporting means.
Figure 9:
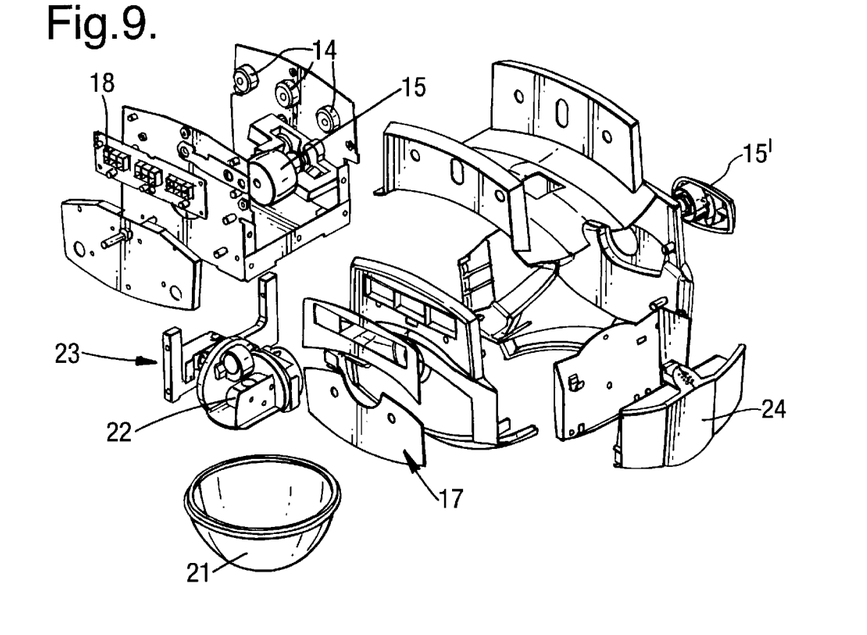
FIG. 9 is an exploded view of the laser unit and its housing, according to the invention.

FIG. 6 illustrates a chassis of the laser unit housing 9, said chassis denoted by reference numeral 12. It will be noted both from FIG. 2 and from FIG. 6, as well as from FIGS. 9 and 10, that said chassis is provided with suitably two sets 13, 14 of rollers which enable the housing 9 to move smoothly along e.g. the supporting member 7, as clearly visualized from viewing FIG. 6. Releasable brake means 15 are provided within said laser unit housing 9, as shown on FIG. 6, said brake means having a releasing mechanism 15'. The brake means is in the form of roller means 15 rotatably bearing against and thus being position-fixable relative to a profiled face 7' of e.g. said supporting means 7. Further, adjustment means 16 is provided for fine adjustment of the position of the laser unit housing along e.g. the supporting means 7 by rotating the roller 15. The housing 9 may be provided with a touch pad 17 for selecting the types of the insertion angle values to be successively entered, and to be displayed on a display 18. Such a touch pad could be of any suitable kind. There is e.g. provided an angle value setting knob 20, e.g. of a pulse counting type in order to adjust to the respective insertion angle values and display such values on the display 18. The housing 9 has a laser beam transparent dome 21 in order that a laser beam from a laser device 22 in the laser unit 23 may exit. On FIG. 9, reference numeral 24 denotes a battery of rechargeable or non-chargeable type.

Figure 10:
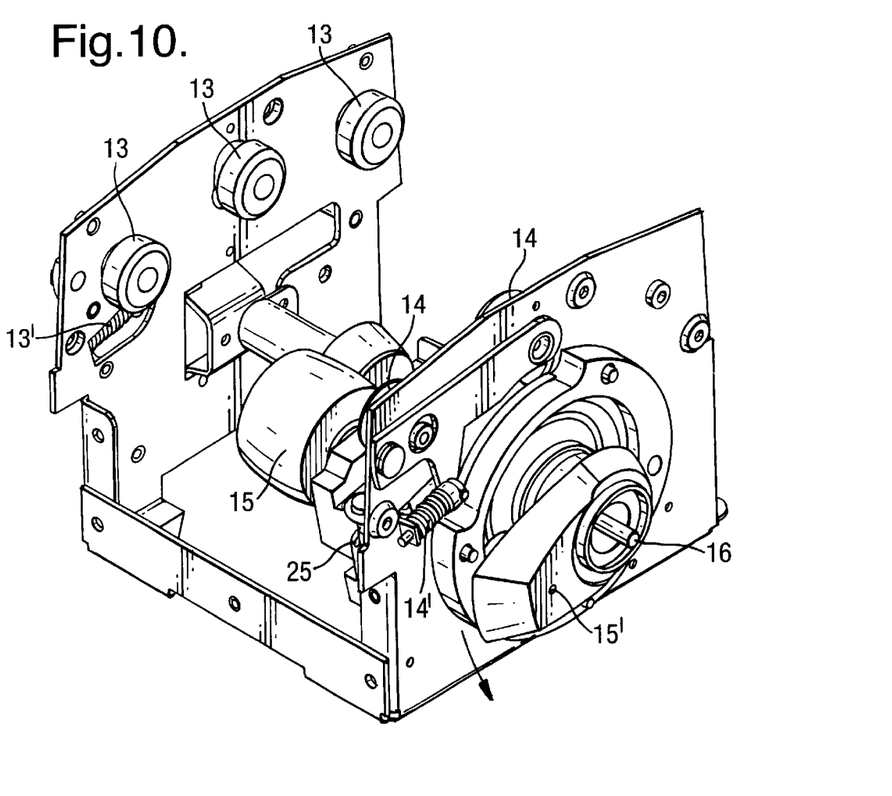
FIG. 10 shows in a greater detail a chassis part of the laser unit, according to the invention.

Suitably, at least some of the rollers 13 and 14 are spring loaded, e.g. using springs 13', 14' as shown on FIG. 10. Spring means 25 may also be provided for the releasable brake means 15.

Figure 7:
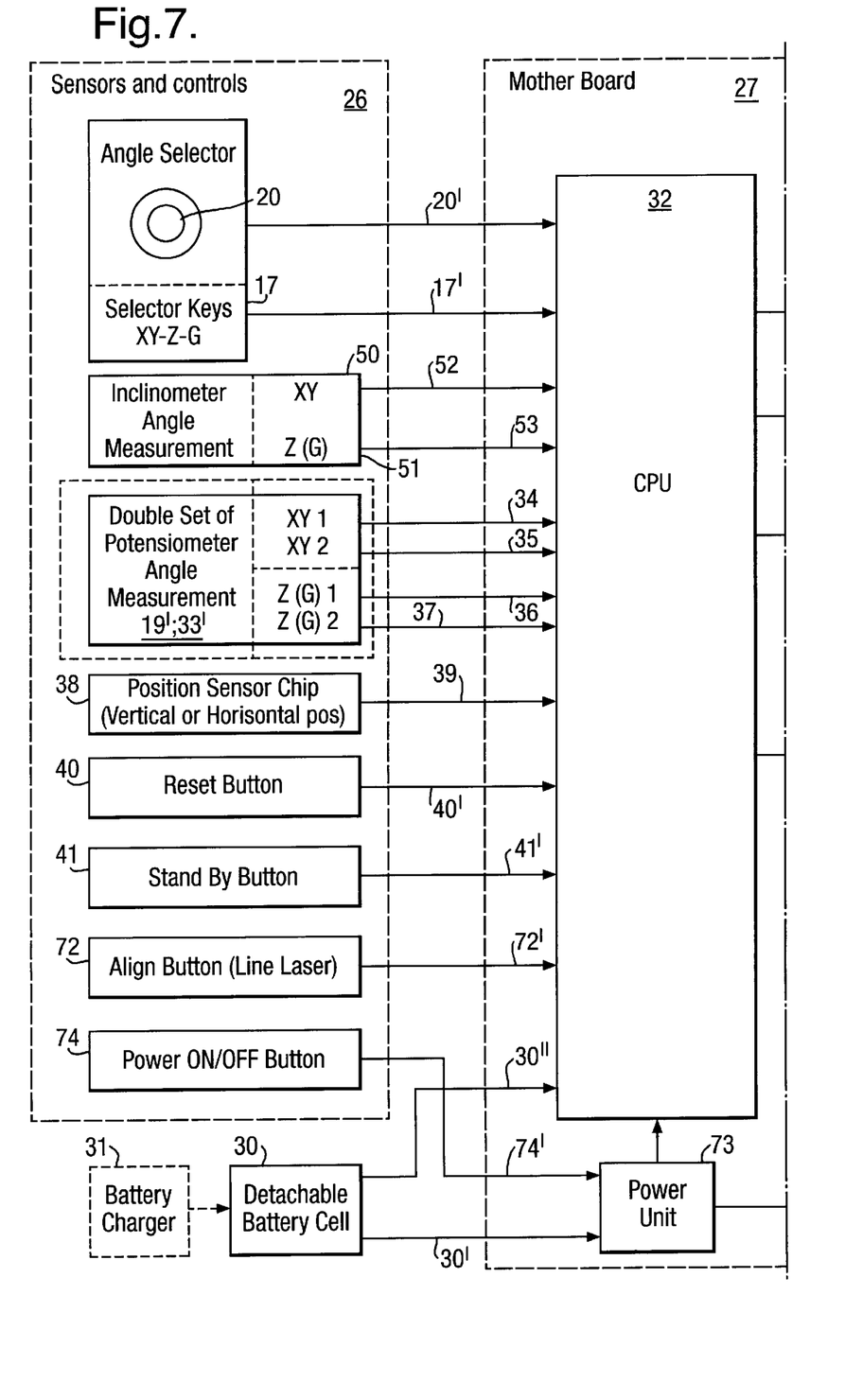
FIG. 7 is a block diagram showing operational components used in carrying out the invention.

FIG. 7 illustrates the various operational elements which are included in the apparatus, according to the present invention. Mainly there is provided sensors and controls 26, a mother board 27, a control and laser system 28, a drive system 29 in addition to battery 30 with the possibility of a battery charger 31. As mentioned above insertion angle values are in the craniocaudal direction and transverse direction using a CT or MR tomography machine. By e.g. using the touch pad 17 and the value adjuster 20, it is possible to indicate the various selector key settings for different planes and directions, i.e. X/Y coordinates, Z coordinates and possibly gravity coordinate. The signals from the angle selector and the selector keys 17 are fed via lines 20', 17' into a processor 32 CPU).

Figure 15:
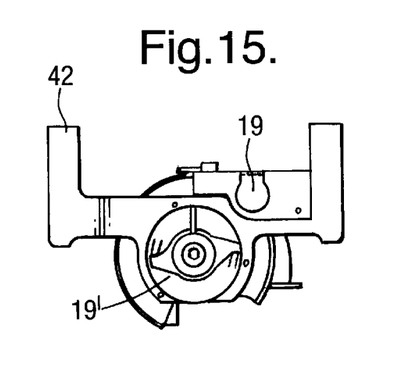
Figure 16:
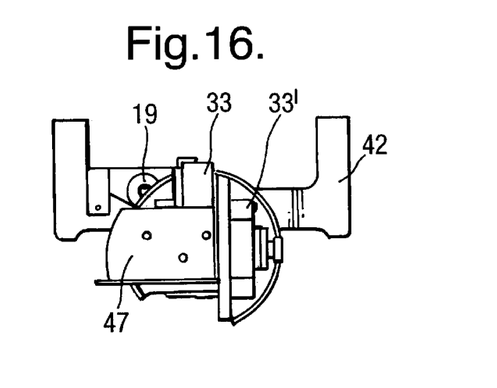

As shown on FIGS. 15 and 16 there is in connection with motor means 19, 33 provided angle measurement means, suitably in the form of a first and second potentiometer 19', 33'. If the motor 19, 33 is e.g. a stepper motor, then such a double set of potentiometer angle measurement devices 19', 33'may be considered redundant. However, it is according to a preferred embodiment of the invention provided such a set of potentiometers for providing coordinate values via signal lines 34, 35, 36, 37 into the processor 32 and to provide for accurate feedback signals. In order to recognize on which housing supporting means the laser unit housing 9 is present, a position sensor chip 38 is provided, delivering signals to the processor 32 via line 39. A reset button 40 is provided for resetting previously set values in order to be able to insert new values through use of the angle selector 20 and the selector keys 17. Further, in order to keep the apparatus in a standby state, a standby button 41 is suitably provided.

On FIG. 7 it will be denoted that there is an aligning button 72. Pushing said button 72 will trigger the line laser 49 to emit a laser light plane and thus create a laser line along said bed 54. Both the reset button 40, the standby button 41 and the line laser button 72 communicate with the processor 32 via respective lines 40', 41' and 72'. Also, there is within the mother board 27 provided a power unit 73 which receives power from the battery cell 30 and can be turned on and off by means of a button 74 communicating with the power unit 73 via line 74'. The battery cell 30 communicates with the power unit 73 via lines 30'. Further, the mother board receives power directly from the battery cell 30 via line 30".

Figure 8:
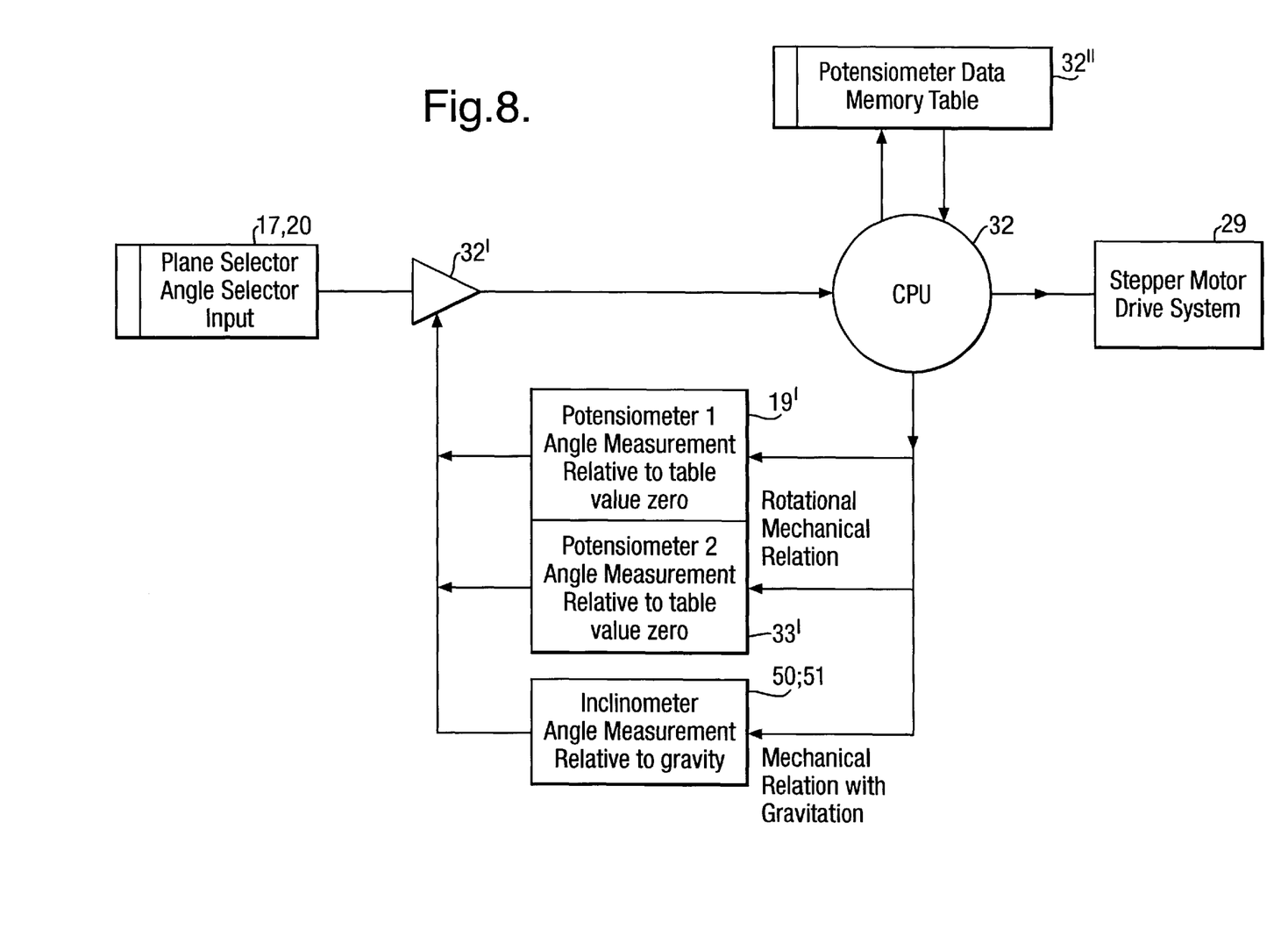
FIG. 8 is a block schematic diagram showing feedback loops for use with the apparatus, according to the invention.

On FIG. 8 there is shown schematically a feedback loop for rotational mechanical relationship and mechanical relationship with gravitation. It will be noted that a plane selector and angle selector input is provided from the previously described means 17, 20 and input to a comparator amplifier 32' forming part of the processor 32. A potentiometer data memory table 32" is provided also within said processor 32 and when the motor drive system 29 operates, the potentiometers 19' and 33' will operate in order to provide a feedback information about the turning of the motors 19, 33. Further, the inclinometers 50, 51, will carry out an angle measurement relative to gravity and the signal outputs from the devices 19', 33', 50 and 51 are input to the comparator amplifier 32' and compared with the inputs from the selectors 17, 20. Further, the potentiometer data memory table could contain any required pre-settings and adjustment values. As soon as the processor 32 detects certain threshold values reached, the motor drive system will suitably be brought to a halt.

Figure 11:
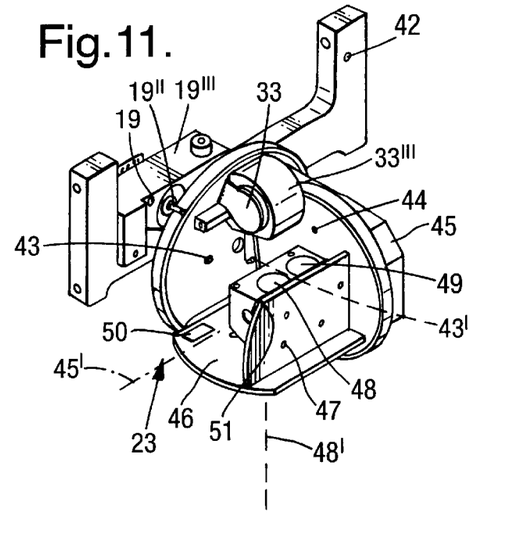
FIGS. 11, 12, 13, 14, 15, and 16 are perspective view from above, bottom plan view, top plan view, front view, view from one side, and view from other side of the laser unit carrying laser device.
Figure 12:
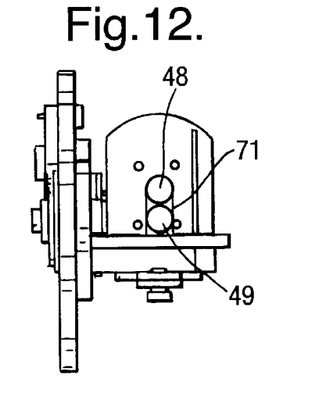
Figure 13:
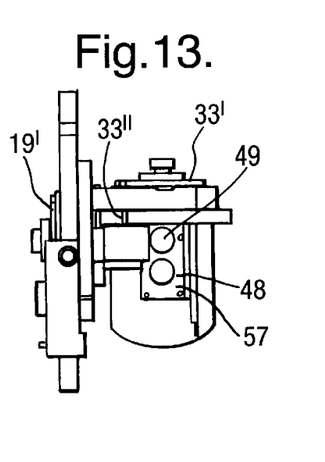
Figure 14:
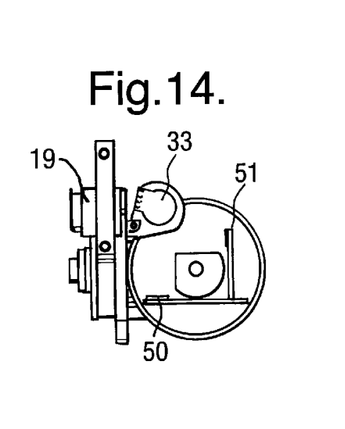

With reference to FIGS. 11–16, there are provided first attachment means 42 on the laser unit housing 9, the assembly shown on FIG. 11 constituting the laser unit 23. The attachment means 42 supports a first rotation member 19 in the form of a motor 19. Further, the first rotation member 43 supports a second rotation means 33 in order to enable rotation of a second rotation member 44 relative to a second attachment means 45 attached to the first rotation member 43. The second rotation member 45 has second rotation axis 45' at right angles to the first rotation axis 43'.

First and second inclinometer supporting means 46, 47 are mounted at right angles to each other and attached to a surface of the second rotation member 44 at right angles thereto. The laser unit 23 has an insertion point laser 48 as well as suitably a line laser device 49 forming a line laser unit. The laser device is suitably attached to the second rotation member 44 in such a way that the laser beam 48' will lie along an axis intersecting an intersection point between said first and second rotation axis 43, 45' and at right angles thereto. First inclinometer means 50 is installed on first inclinometer supporting means 46 and second inclinometer means 51 is installed on the second inclinometer supporting means 47. The inclinometer 50, 51 provide signal values via lines 52, 53 to the processor 32 as a function of two- or three-dimensional orientation direction of the laser unit housing relative to direction of gravitation. The double set of potentiometers form first and second encoder means which are cooperative with the motors 19, 33, respectively, for feedback of rotary position information to the processor 32. Within the processor 32 there is provided comparator means for comparing set calculated instrument insertion angle values provided from the input device 17, 20 and 18, with encoder signal values derived as feedback information from the devices 19', 33' and the inclinometer signal values on lines 52 and 53. The comparator means within the processor 32 will suitably be capable of inhibiting an operation of the motors 19 and 33 when the encoder signal values and the inclinometer signal values reach threshold values, respectively, related to said insertion angle values and any deviations away from the direction of gravitation. It is important in the embodiment as shown on e.g. FIG. 1 to have in particular the supporting means 7 at right angles to the craniocaudal direction. For such purpose, the line laser device 49 provides a laser beam created line for aligning the laser unit housing relative to a craniocaudal direction of a movable bed 54 supporting the body 11 of e.g. a human being, the laser created line being labelled by reference numeral 55 in FIG. 3 and reference numeral 56 in FIG. 4. It will be appreciated that in effect, the line laser device really provides a light plane created by the laser device as denoted by reference numerals 55' and 56', respectively. Such a light plane 55' is also schematically indicated on FIG. 1.

In a preferred, but non-limiting embodiment of the invention, the laser device 48 is mounted on suitably the first of the inclinometer supporting means 46, although it could equally well have been installed on the second inclinometer supporting means 47. In a preferred embodiment the laser device 48 and the line laser device 49 are mechanically interconnected as a rigid unit, suitably in a common mounting block 57. As shown on FIG. 7 both the point laser 48 and the line laser 49 have a laser driver 58 intermediate said processor 32 and the lasers 48, 49.

As shown on FIG. 7 the motors 19, 33 operate on the first and second rotation members 43, 44, respectively. As shown on FIGS. 11, 14, 15, and 16 in particular, it is seen that said rotation members have a substantially fixed radius of curvature over at least a substantial part of a circumference thereof. The motors 19, 33 have in a first embodiment a respective shaft 19", 33" capable of being in rotational and frictional engagement with said at least substantial part of the circumference of the respective rotation member 43, 44. Suitably, said shaft 19", 33" is provided with a friction creating material. Alternatively, or in addition, said at least substantial part of said circumference is provided with a friction creating material. The frictional engagement is suitably adjustable or maintained through said shaft resiliently bearing against said at least substantial part of the circumference. The way to provide such resiliency would be to have the motors 19, 33 resiliently installed in a respective motor housing 19′′′, 33′′′.

Figure 17:
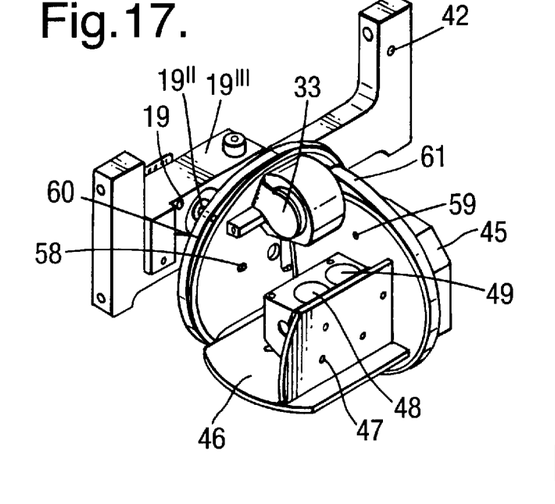
FIGS. 17, 18, and 19 show variants of the embodiment shown on FIGS. 11–16.

In an alternative as shown on FIG. 17, the first and second rotation members 58, 59 have a fixed radius of curvature over the full circumference thereof, respectively. Motor means 19, 33 are provided as shown and described in connection with FIG. 11 and the shafts of the respective motors 19, 33 are capable of being in rotational, frictional engagement with a belt 60, 61, respectively, said belt 60 and 61 being in contact with a substantial part of said circumference of said first and second rotation members 58, 59.

Figure 18:
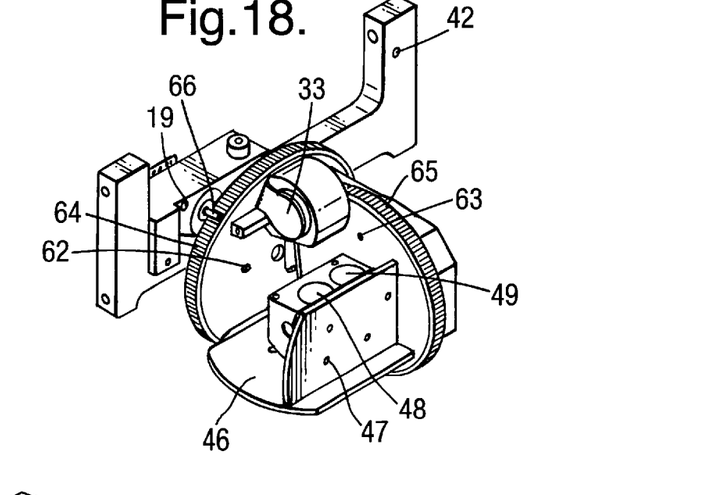

In further embodiment shown on FIG. 18, it will also be noted that the first and second rotation members, here denoted by reference numerals 62 and 63, have a fixed radius of curvature over at least a substantial part of a circumference thereof, and have gear teeth 64 extending therealong, respectively. The motor 19 is shown having a shaft 66 with a gear at the end capable of being in rotational, frictional engagement with said gear teeth 64. Similarly, a shaft on the second motor 33 will similarly have a gear (not shown) which is capable of being in rotational, frictional engagement with gear teeth 65 on the second rotation member 63.

Figure 19:
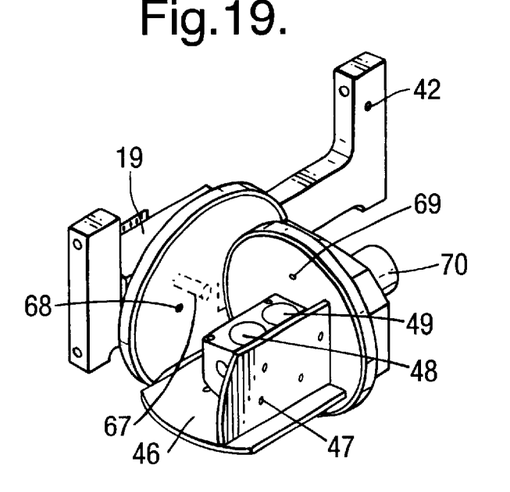

In the embodiment shown on FIG. 19, the first motor 19 has its shaft 67 directly connected to the rotation central axis of the first rotation member 68. Similarly, the second rotation member, here labelled 69, is directly connected to a shaft (not shown) of an electric motor 70.

Although any suitable type of electric motor could be used, it is preferred to use a stepper motor.

Suitably said first and second inclinometer supporting means 46, 47 are circuit board members mounted at right angles to each other and attached to a surface of the second rotation member at right angles thereto. As shown on FIG. 12, a hole is provided for laser beam exit from the laser device 48 as well as from the line laser device 49. Although the line laser device 49 is preferably attached to either of the inclinometer supporting means 46, 47, in the preferred embodiment attached to the means 46, said line laser device could equally well be attached directly to the second rotary member, such as member 44, 59, 63 or 69.

What is claimed is:

1. An apparatus for assisting percutaneous light beam guided surgical activity into a human or animal body based on calculated craniocaudal and transverse related insertion angles for an injection instrument, such as a syringe needle or biopsy means, relative to a target inside said body, said apparatus having means for providing at least a laser beam from a laser device in a laser unit for assisting guided instrument injection into said body, said laser unit having a housing being positionable along a laser unit supporting means and lockable thereto, said laser unit having means for adjusting the direction of said laser beam relative to said body based on said calculated insertion angles, wherein said apparatus further comprises within said laser unit housing:

first attachment means on said laser unit housing for rotatably supporting a first rotation member of said laser unit;

first rotation means attached to said first attachment means for rotating said first rotation member relative to said first attachment means about a first rotation axis;

second attachment means attached to said first rotation member for rotatably supporting a second rotation member, said second rotation member having a second rotation axis at right angles to the first rotation axis;

second rotation means mounted on said first rotation member for rotating said second rotation member relative to said second attachment means;

first and second inclinometer supporting means mounted at right angles to each other and attached to a surface of said second rotation member at right angles thereto;

said laser unit having said laser device attached to said second rotation member in such a way that the laser beam is along an axis intersecting an intersection point between said first and second rotation axis and at right angles thereto;

first inclinometer installed on said first inclinometer supporting means and second inclinometer installed on said second inclinometer supporting means, said inclinometer providing signal values as a function of two- or three-dimensional orientation directions of said laser unit housing relative to direction of gravitation;

first and second encoding means cooperative with said first and second rotation means, respectively for feedback of rotary position information thereof; and comparing means for comparing set calculated instrument insertion angle values, provided from an input device, with encoder signal values derived from said feedback information and said inclinometer signal values, said comparing means inhibiting an operation of said first and second rotation means when said encoder signal values and said inclinometer signal values reach threshold values, respectively related to said set insertion angle values and direction of gravitation.

2. Apparatus according to claim 1, comprising a line laser unit having a line laser device which provides a laser beam created line for aligning said laser unit housing relative to a craniocaudal direction of a movable bed supporting said body.

3. Apparatus according to claim 1, wherein said laser device is mounted on said first or second inclinometer supporting means.

4. Apparatus according to claim 3, wherein said laser device and said line laser device are mechanically interconnected as a rigid unit.

5. Apparatus according to claim 2, wherein said line laser device is mounted on said first or second inclinometer supporting means.

6. Apparatus according to claim 5, wherein said laser device and said line laser device are mechanically interconnected as a rigid unit.

7. The apparatus of claim 1, wherein said first and second rotation member have a fixed radius of curvature over at least a substantial part of a circumference thereof, respectively, wherein said first and second rotation means each comprises an electric motor and a shaft thereof, said shaft capable of being in rotational, frictional engagement with said at least substantial part of said circumference.

8. The apparatus of claim 7, wherein said shaft is provided with a friction creating material.

9. The apparatus of claim 7, wherein said at least substantial part of said circumference is provided with a friction creating material.

10. The apparatus of claim 7, wherein said frictional engagement is adjustable or maintained through said shaft resiliently bearing against said at least substantial part of said circumference.

11. The apparatus of claim 7, wherein said electric motor is a stepper motor.

12. The apparatus of claim 1, wherein said first and second rotation members have a fixed radius of curvature over the full circumference thereof, respectively, wherein said first and second rotation means each comprises an electric motor and a shaft thereof, said shaft capable of being in rotational, frictional engagement with a belt in contact with a substantial part of said circumference.

13. The apparatus of claim 12, wherein said electric motor is a stepper motor.

14. The apparatus of claim 1, wherein said first and second rotation members have a fixed radius of curvature over at least a substantial part of a circumference thereof and have gear teeth extending therealong, respectively, wherein said first and second rotation means each comprises an electric motor and a shaft thereof, said shaft having a gear capable of being in rotational, frictional engagement with said gear teeth.

15. The apparatus of claim 14, wherein said electric motor is a stepper motor.

16. The apparatus of claim 1, wherein said first and second rotation members are each directly connected to a shaft of an electric motor.

17. The apparatus of claim 16, wherein said electric motor is a stepper motor.

18. The apparatus of claim 1, wherein said first and second inclinometer supporting means are circuit board members mounted at right angles to each other and attached to a surface of said second rotation member at right angles thereto, one of said circuit board members having a hole for laser beam exit from said laser device.

19. The apparatus of claim 2, wherein said first and second inclinometer supporting means are circuit board members mounted at right angles to each other and attached to a surface of said second rotation member at right angles thereto, one of said circuit board members having a hole for laser beam exit from said line laser device.

20. The apparatus of claim 2, wherein said line laser device is attached to said second rotary member or to one of said inclinometer supporting means.

21. An apparatus for assisting percutaneous light beam guided surgical activity into a human or animal body based on calculated craniocaudal and transverse related insertion angles for an injection instrument, such as a syringe needle or biopsy means, relative to a target inside said body, said apparatus having means for providing a laser beam from at least one laser unit for assisting guided instrument injection into said body, said laser unit having a housing being positionable along a housing supporting means and lockable thereto, said laser unit having means for adjusting the direction of said laser beam relative to said body based on said calculated insertion angles, wherein said apparatus further comprises:

releasable brake means within said laser unit housing, said brake means in the form of roller means rotatably bearing against and position-fixable relative to a profiled face of said laser unit housing supporting means; and position adjustment means for fine adjustment of a position of said laser unit housing on said supporting means.

22. The apparatus of claim 21, wherein said laser unit housing supporting means comprises:

a movable base member, said base member being position lockable relative to a floor;

an upright, first housing supporting member extending upwardly from said base member;

a second housing supporting member extending from a top of said first housing supporting member at right angles thereto, and a curved transition member extending between said first and second laser unit housing supporting members for supporting the laser unit and its housing in movement between said first and second laser unit housing supporting members, whereby said laser unit housing is movable along said first and second head supporting members and selectively lockable thereto.

23. The apparatus of claim 21, wherein said first laser unit housing supporting member is pivotable about its axis relative to said base member, and lockable thereto.

* * * * *